(12) United States Patent
Fairbrother et al.

(10) Patent No.: US 8,623,372 B2
(45) Date of Patent: *Jan. 7, 2014

(54) **ANTIBODIES FOR PREVENTING AND TREATING ATTACHING AND EFFACING *ESCHERICHIA COLI* (AEEC) ASSOCIATED DISEASES**

(75) Inventors: John M. Fairbrother, Saint-Hyacinthe (CA); Josée Harel, Saint-Bruno (CA); Isabelle Batisson, Clermont-Ferrand (FR); Francis Girard, Saint-Hyacinthe (CA); Marie-Pierre Guimond, Montréal (CA)

(73) Assignee: Valorisation-Recherche, Societe En commandite, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/732,419

(22) Filed: Mar. 26, 2010

(65) Prior Publication Data

US 2010/0183627 A1 Jul. 22, 2010

Related U.S. Application Data

(60) Continuation of application No. 12/257,420, filed on Oct. 24, 2008, now Pat. No. 7,727,531, which is a division of application No. 10/471,914, filed as application No. PCT/CA02/00353 on Mar. 14, 2002, now Pat. No. 7,445,782.

(30) Foreign Application Priority Data

Mar. 15, 2001 (CA) .................................... 2339436

(51) Int. Cl.
*A61K 39/40* (2006.01)

(52) U.S. Cl.
USPC .................. 424/169.1; 424/130.1; 424/157.1; 424/164.1; 530/388.4; 800/6

(58) Field of Classification Search
None
See application file for complete search history.

(56) References Cited

U.S. PATENT DOCUMENTS 4,550,019 A * 10/1985 Polson ........................ 424/157.1
4,748,018 A 5/1988 Stolle et al. ................ 424/157.1
(Continued)

FOREIGN PATENT DOCUMENTS

CA 2078716 9/1992
EP 0873755 * 10/1988
(Continued)

OTHER PUBLICATIONS

Adu-Bobie, J et al, Journal of Clinical Microbiology, vol. 36(3), pp. 662-668, Mar. 1998, Dection of Intimains alpha, beta, gamma and delta, four intimin derivatives expressed by attaching nd Effacing Microbial Pathogens.*

(Continued)

*Primary Examiner* — Albert Navarro
*Assistant Examiner* — Ginny Portner
(74) *Attorney, Agent, or Firm* — Myers Bigel Sibley & Sajovec, P.A.

(57) ABSTRACT

The present invention relates to antibodies immunologically specific for an attaching and effacing *Escherichia coli* (AEEC) virulence-associated protein, products, compositions and methods and to their use thereof in the prevention of an AEEC infection in a mammal. The antibody of the invention is immunologically specific for an AEEC virulence-associated protein and is capable of preventing an in vivo AEEC intestinal infection when administered to a mammal. The antibody of the invention is preferably useful for preventing the development of A/E intestinal lesions associated with the AEEC. This is achieved by preferably using IgY antibodies immunologically specific for one or more AEEC virulence-associated proteins, such as Eae, Tir, EspA and Paa.

11 Claims, 9 Drawing Sheets

(56) References Cited

U.S. PATENT DOCUMENTS

| | | | | |
|---|---|---|---|---|
| 5,367,054 A | * | 11/1994 | Lee | 530/359 |
| 5,585,098 A | * | 12/1996 | Coleman | 424/157.1 |
| 5,741,489 A | * | 4/1998 | Pimentel | 424/157.1 |
| 5,798,260 A | * | 8/1998 | Tarr et al. | 435/252.3 |
| 5,932,250 A | | 8/1999 | Stolle et al. | |
| 5,972,721 A | | 10/1999 | Bruno et al. | 436/526 |
| 6,162,441 A | * | 12/2000 | Chae et al. | 424/241.1 |
| 6,204,004 B1 | * | 3/2001 | Kaper et al. | 435/7.37 |
| 6,291,435 B1 | * | 9/2001 | Yanmaele et al. | 514/25 |
| 6,635,259 B2 | | 10/2003 | Kaper et al. | 424/241.1 |
| 6,942,861 B2 | | 9/2005 | McKee et al. | 424/169.1 |
| 7,208,574 B1 | | 4/2007 | Finlay et al. | 530/350 |
| 7,241,443 B1 | * | 7/2007 | Nash et al. | 424/130.1 |
| 7,250,261 B2 | | 7/2007 | Leong et al. | 435/6 |
| 7,300,659 B2 | | 11/2007 | Finlay et al. | 424/234.1 |
| 7,355,092 B2 | | 4/2008 | Marquardt et al. | 800/4 |
| 7,445,782 B2 | * | 11/2008 | Fairbrother et al. | 424/164.1 |
| 7,727,531 B2 | * | 6/2010 | Fairbrother et al. | 424/157.1 |
| 2002/0006407 A1 | | 1/2002 | McKee et al. | 424/184.1 |
| 2002/0012658 A1 | | 1/2002 | Williams et al. | 424/93.2 |
| 2002/0115829 A1 | | 8/2002 | Finlay et al. | 530/350 |
| 2002/0122803 A1 | | 9/2002 | Kisic et al. | 424/164.1 |
| 2002/0136727 A1 | | 9/2002 | Nash et al. | 424/150.1 |
| 2002/0147313 A1 | | 10/2002 | Yoder et al. | 530/388.1 |
| 2002/0160020 A1 | | 10/2002 | Finlay et al. | 424/257.1 |
| 2003/0185856 A1 | | 10/2003 | Lee et al. | 424/203.1 |
| 2004/0258664 A1 | | 12/2004 | Pitcovski et al. | 424/93.2 |
| 2005/0186217 A1 | | 8/2005 | Emery et al. | 424/190.1 |
| 2005/0226861 A1 | | 10/2005 | Nash et al. | 424/130.1 |
| 2005/0255092 A1 | | 11/2005 | Rehberger et al. | 424/93.46 |
| 2006/0223986 A1 | | 10/2006 | Chiou | 530/387.1 |

FOREIGN PATENT DOCUMENTS

| | | | |
|---|---|---|---|
| EP | 0873755 | | 10/1998 |
| EP | 0873755 | | 10/1999 |
| JP | 10-298105 | | 11/1998 |
| WO | 97/40063 | | 10/1997 |
| WO | WO 9740063 | | 10/1997 |
| WO | 98/14209 | | 4/1998 |
| WO | 99/24576 | * | 5/1999 |
| WO | 9924576 | | 5/1999 |
| WO | WO 9924576 | | 5/1999 |
| WO | WO 9941614 | | 8/1999 |
| WO | WO 0052055 | | 9/2000 |
| WO | 02/053179 | | 7/2002 |

OTHER PUBLICATIONS

Ogierman, M. A. et al, Infection and Immunity, vol. 68(9), pp. 5344-5353, Sep. 2000, Up-Regulation of both Intimin and eae-independent Adherence of Shiga toxigenic *Escherichia coli* O157 by ler and Phenotypic Impact of a Naturally Occuring ler mutation.*

Kuhne, S.A. et al, Journal of Clinical Microbiology, Jul. 2004, vol. 42(7), pp. 2966-2976, Isolation of recombinant antibodies against EspA and Intimin or *E.coli* O157:H7.*

Frankel, Gad et al, Molecular Microbiology, 1998, vol. 30(5), pp. 911-921, Enteropathogenic and enterohaemorrhagic *Escherichia coli*: more subversive elements.*

Kenny, Brendan et al, Cell, vol. 91, pp. 511-520, Nov. 14, 1997, Enteropathogenic *E.coli* (EPEC) transfers its receptor for intimate adherence into Mammalian cells.*

Sanches, M.I. et al, Journal of Pediatric Gastroenterology and Nutrition, vol. 30(1), Jan. 2000, pp. 73-77, Human Colostrum and Serum contain antibodies reactive to the Intimin-Binding Region of the Enteropathogenic *Escherichia coli* Translocated Intimin Receptor.*

Review—Chicken Antibodies, pp. 1-2, IgY-Prophylaxis Therapy and Diagnosis, down loaded from the website for oramune Jul. 18, 2013.*

Batchelor, M et al, The EMBO Journal, vol. 19(11), pp. 2452-2464, 2000, Structural basis for recognition of the translocated intimin receptor (TIR) by intimin from enteropathogenic *Escherichia coli*.*

An H et al. "Distribution of a novel locus called paa (porcine attaching and effacing associated) among enteric *Escherichia coli*" Advances in Experimental Medicine and Biology 2000 US 473:179-184.

Li Y et al. "Human response to *Escherichia coli* O157:H7 infection : antibodies to secreted virulence factors." Infection and Immunity, American Society for Microbiology, Sep. 2000, 68 :5090-5095.

Marquardt R R et al. "Passive protective effect of egg-yolk antibodies against enterotoxigenic *Escherichia coli* k88+ Infection In neonatal and early-weaned piglets", FEMS Immunology and Medical Microb. Apr. 1999, 23:283-288.

Nataro James P et al. "Diarrheagenic *Escherichia coli*", Clinical Microbiology Reviews. Jan. 1998, 11:142-201.

Caprioli et al. "Enterohaemorrhagic *Escherichia coli*: emerging issues on virulence and modes of transmission", *Vet. Res.* 36:289-311 (2005).

Nataro et al. "Diarrheagenic *Escherichia coli*" *Clinical Microbiology Reviews* 11(1):142-201 (1998).

Robinson et al. "Shiga toxin of enterohemorrhagic *Escherichia coli* type 0157:H7 promotes intestinal colonization" *PNAS* 103(25):9667-9672 (2006).

Son et al. "Immunological Characterization of *Esherichia coli* 0157:H7 Intimin y1" *Clinical and Diagnostic Laboratory Immunology* 9(1):46-53 (2002).

Anicetti, Vincent R et al, Immunization Procedures of *E. coli* proteins, Appl. Biochemistry and Biotechnology, vol. 22, pp. 151-168, 1989.

An, Hongyan et al, Distribution of a novel locus call paa (porcine attaching and effacing associated) among enteric *Escherichia coli*, Mechanisms in the pathogenesis of Enteric Diseases 2, 2000, p. 179-184.

Akita, EM et al, J. Immunological Methods, vol. 160, pp. 207-214, 1993, Comparison of four purification methods for the production of immunoglobulins from eggs laid by hens immunized with an enterotoxigenic *E.coli* strain.

Heller, ED, Research in Veterinary Science, vol. 18, pp. 117-120, 1975, The immune response of hens to multiple *Escherichia coli* injections and transfer of immunoglobulin to the egg and hatched chick.

Li, Yuling et al, Infection and Immunity, Sep. 2000, pp. 5090-5095, Human response to *Escherichia coli* O157:H7 infection: antibodies to secreted virulence factors.

Malkinson, M, Immunology, 1965, vol. 9, pp. 311-317, The transmission of passive immunity to *Escherichia coli* from mother to young in the Domestic fowl (*Gallus domesticus*).

Ryu, H et al, Infection and immunity, vol. 69(2), pp. 640-649, Feb. 2001.

Schmidt, P et al, J. Vet. Med. vol. B36, pp. 619-628, 1989, Chicken egg antibodies for Prophylaxis and Therapy of infectious intesinal diseases.

Akita, EM et al, J. Immunol. Methods, 1993, Apr. 2, vol. 160(2), pp. 207-214 (Abstract Only).

Fairbrother, JM et al, Distribution of a novel locus call Paa (porcine attaching and effacing associted) among enteric *Escherichia coli*. Advances in Experimental Medicine and Biology, vol. 473, pp. 179-184, 1999 (Abstract Only).

Batisson et al (Aug. 2003) Infection and Immunity, vol. 71(8), pp. 4516-4525.

Bianchi et al., Parental vaccination of mice and piglets with F4+ *Escherichia coli* suppresses the enteric anti-F4 response upon oral infection, Vaccine, 1996, pp. 199-206, vol. 14 No. 3.

Holmgren, Jan, Mucosal immunity and vaccination, FEMS Microbiology Immunology, 1991, pp. 1-9, vol. 89.

Offit et al., Protection Against Rotavirus-Induced Gastroenteritis in a Murine Model by Passively Acquired Gastrointestinal But Not Circulating Antibodies, Journal of Virology, 1985, pp. 58-64, vol. 54 No. 1.

* cited by examiner

```
                          SEQUENCE LISTING

<160> NUMBER OF SEQ ID NOS: 16

<210> SEQ ID NO 1
<211> LENGTH: 24
<212> TYPE: DNA
<213> ORGANISM: Artificial
<220> FEATURE:
<223> OTHER INFORMATION: PCR primer

<400> SEQUENCE: 1
ggatccgcaa caaccgatca gaat                                              24

<210> SEQ ID NO 2
<211> LENGTH: 24
<212> TYPE: DNA
<213> ORGANISM: Artificial
<220> FEATURE:
<223> OTHER INFORMATION: PCR primer

<400> SEQUENCE: 2
ctcgagtttt acacaaacag gaaa                                              24

<210> SEQ ID NO 3
<211> LENGTH: 18
<212> TYPE: DNA
<213> ORGANISM: Artificial
<220> FEATURE:
<223> OTHER INFORMATION: PCR primer

<400> SEQUENCE: 3
ggatccaatg gtgaaaat                                                     18

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
aagctttttt acacaaacag g                                                 21

<210> SEQ ID NO 5
<211> LENGTH: 24
<212> TYPE: DNA
<213> ORGANISM: Artificial
<220> FEATURE:
<223> OTHER INFORMATION: PCR primer

<400> SEQUENCE: 5
ggatccatgg atacatcaac tgca                                              24

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
```

-continued ctcgagttta ccaagggata                    20

<210> SEQ ID NO 7
<211> LENGTH: 24
<212> TYPE: DNA
<213> ORGANISM: Artificial
<220> FEATURE:
<223> OTHER INFORMATION: PCR primer

<400> SEQUENCE: 7
ggatccatga atactattga ttat               24

<210> SEQ ID NO 8
<211> LENGTH: 25
<212> TYPE: DNA
<213> ORGANISM: Artificial
<220> FEATURE:
<223> OTHER INFORMATION: PCR primer

<400> SEQUENCE: 8
ctcgagaacc agctaagcga accga              25

<210> SEQ ID NO 9
<211> LENGTH: 24
<212> TYPE: DNA
<213> ORGANISM: Artificial
<220> FEATURE:
<223> OTHER INFORMATION: PCR primer

<400> SEQUENCE: 9
ggatccatgc ttaatgtaaa tagc               24

<210> SEQ ID NO 10
<211> LENGTH: 24
<212> TYPE: DNA
<213> ORGANISM: Artificial
<220> FEATURE:
<223> OTHER INFORMATION: PCR primer

<400> SEQUENCE: 10
ctcgagaact cgaccactaa caat               24

<210> SEQ ID NO 11
<211> LENGTH: 21
<212> TYPE: DNA
<213> ORGANISM: Artificial
<220> FEATURE:
<223> OTHER INFORMATION: PCR primer

<400> SEQUENCE: 11
gagctcatgc ctattggtaa t                  21

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
aagcttaacg aaacgtgcgg                    20

<210> SEQ ID NO 13
<211> LENGTH: 22
<212> TYPE: DNA
<213> ORGANISM: Artificial
<220> FEATURE:

```
<223> OTHER INFORMATION: PCR primer

<400> SEQUENCE: 13
ggatcccttt atctgcgaaa aa                                              22

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
ctcgagagtg cctttcctgg                                                 20

<210> SEQ ID NO 15
<211> LENGTH: 19
<212> TYPE: DNA
<213> ORGANISM: Artificial
<220> FEATURE:
<223> OTHER INFORMATION: PCR primer

<400> SEQUENCE: 15
ggatccatga ggaacataa                                                  19

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
ctcgagagtg cctttcctgg                                                 20
```

ANTIBODIES FOR PREVENTING AND TREATING ATTACHING AND EFFACING *ESCHERICHIA COLI* (AEEC) ASSOCIATED DISEASES

RELATED APPLICATIONS

This application is a Continuation Application of U.S. application Ser. No. 12/257,420, filed Oct. 24, 2008 now U.S. Pat. No. 7,727,531, allowed, which is a Divisional Application of U.S. application Ser. No. 10/471,914, filed Nov. 12, 2003, now U.S. Pat. No. 7,445,782, which claims priority under 35 U.S.C. §371 from PCT Application No. PCT/CA02/00353, filed in English Mar. 14, 2002, which claims the benefit of Canadian Application No. 2,339,436, filed Mar. 15, 2001, the disclosures and contents of which are incorporated by reference herein in their entireties.

FIELD OF THE INVENTION

The present invention relates to antibodies immunologically specific for an attaching and effacing *Escherichia coli* (AEEC) virulence-associated protein and to the use thereof in the prevention of an AEEC infection in a mammal.

BACKGROUND OF THE INVENTION

*Escherichia coli* is associated with a wide variety of intestinal diseases in human and in animals. Some pathogenic *E. coli* produces attaching and effacing (A/E) lesions, characterized by intimate bacterial adherence to enterocytes and disruption of the underlying cytoskeleton. Such isolates have been termed A/E *E. coli* (AEEC).

Reports have shown that A/E lesions are characteristic of enteric pathogens of humans such as enteropathogenic *E. coli* (EPEC) responsible for severe childhood diarrhea in the developing countries, and enterohemorrhagic *E. coli* (EHEC) causing hemorrhagic colitis and hemolytic uremic syndrome (HUS). A/E lesions have also been associated with diarrhea in different animal species such as rabbits, calves, dogs, cats, lambs, and pigs.

A/E lesions result from the intimate bacterial adherence to the apical surface of the enterocytes and activation of several chromosomal gene products that interact with components of the host cell. Such gene products are commonly called AEEC virulence-associated proteins. Examples of these virulence-associated proteins are the intimin (Eae) and the secreted proteins Tir (translocated intimin receptor), EspA, EspD, and EspB.

Currently, the only approach to the control and treatment of AEEC-associated diseases is the use of antibiotics, an approach which is becoming less and less desirable due to problems of bacterial resistance and antibiotic residues. Therefore, alternative approaches to control post-weaning diarrhea must be sought.

Alternatively, another approach known in the art suggests the use of AEEC virulence-associated proteins as antigens to immunize an animal in order to stimulate antibody production against the related pathogen. However, no indication of the efficacy of this approach has been shown to prevent AEEC infection in a mammal. Examples of such an alternative approach are shown in U.S. Pat. No. 6,204,004 and in international patent applications WO 99/41614; WO 97/40063 and WO 99/24576.

Also known in the art is the use of avian antibodies (IgY) in passive immunization. For instance, WO 00/52055 discloses the use of specific egg yolk IgY antibodies for immunotherapy in animal breeding and animal production. It also discloses the use of IgY antibodies in kits for diagnostics.

U.S. Pat. No. 5,932,250 is directed to the treatment of vascular disorders particularly arteriosclerosis and atherosclerosis in warm-blooded animals. More specifically, this U.S. patent discloses methods of controlling cholesterol levels, lipid deposits, and the development of atheromatous lesions in warm-blooded animals by the ingestion of egg products containing IgY antibodies raised against *Escherichia coli* proteins.

U.S. Pat. No. 6,162,441 discloses a method for producing anti-*E. coli* O157 IgY antibodies in egg-laying hens.

The problem with WO 00/52055, U.S. Pat. No. 5,932,250 and U.S. Pat. No. 6,162,441 is that the in vivo efficacy of the IgY produced has not been demonstrated. Indeed, none of these contain evidence with respect to the feasibility of an approach consisting of administering to a mammal, an antibody immunologically specific for an AEEC virulence-associated protein for preventing an in vivo AEEC intestinal infection. Therefore, there is still a need for antibodies, egg products and methods for the prevention or treatment of AEEC-mediated diseases.

SUMMARY OF THE INVENTION

The present invention relates to antibodies immunologically specific for an attaching and effacing *Escherichia coli* (AEEC) virulence-associated protein and to the use thereof in the prevention of an AEEC infection in a mammal.

According to a first aspect, the invention relates to an antibody immunologically specific for an AEEC virulence-associated protein, the antibody being capable of preventing an in vivo AEEC intestinal infection when administered to a mammal.

In a preferred embodiment, the antibody of the invention is resistant to gastrointestinal digestion. More preferably, the antibody of the invention is an IgY antibody.

The antibody of the invention is preferably capable of preventing the adhesion of the AEEC to the intestine of the mammal. Even more preferably, the antibody of the invention is capable of preventing the development of attaching and effacing (A/E) intestinal lesions associated with the AEEC. This aspect of the invention is achieved by particularly using antibodies immunologically specific for one or more AEEC virulence-associated proteins, such as Eae, Tir, EspA and Paa.

According to another aspect, the invention relates to a fowl egg and an isolated yolk of such egg containing an antibody as defined hereinabove.

According to a further aspect, the invention relates to a composition which comprises a biologically acceptable vehicle or carrier and an antibody as defined above, a fowl egg as defined above; and/or its isolated yolk as defined above.

According to another aspect, the invention relates to a food additive which comprises an antibody as defined above, a fowl egg as defined above, a yolk fraction as defined above, and/or a composition as defined above.

According to a further aspect, the invention relates a process for obtaining an antibody as defined herein above, the process comprising the steps of:
  a) actively immunizing a fowl hen for eliciting the production of antibodies in an egg of the hen; and
  b) recovering the antibodies from the egg.

According to a further aspect, the invention relates to a method for preventing an attaching and effacing *Escherichia coli* (AEEC) infection in a mammal. The method comprises the step of orally administering to the mammal an antibody as defined above, a fowl egg as defined above and/or an isolated yolk as defined above.

A major advantage of the invention is that it provides antibodies, products, compositions and methods useful and efficient for the prevention of an AEEC infection in a mammal.

Furthermore, it is particularly an advantage that the antibodies, products, compositions and methods of the invention prevent specifically the development of A/E intestinal lesions associated with the AEEC.

Other objects and advantages of the present invention will be apparent upon reading the following non-restrictive description of several preferred embodiments, made with reference to the accompanying drawings.

DETAILED DESCRIPTION OF THE INVENTION

Figure 1:
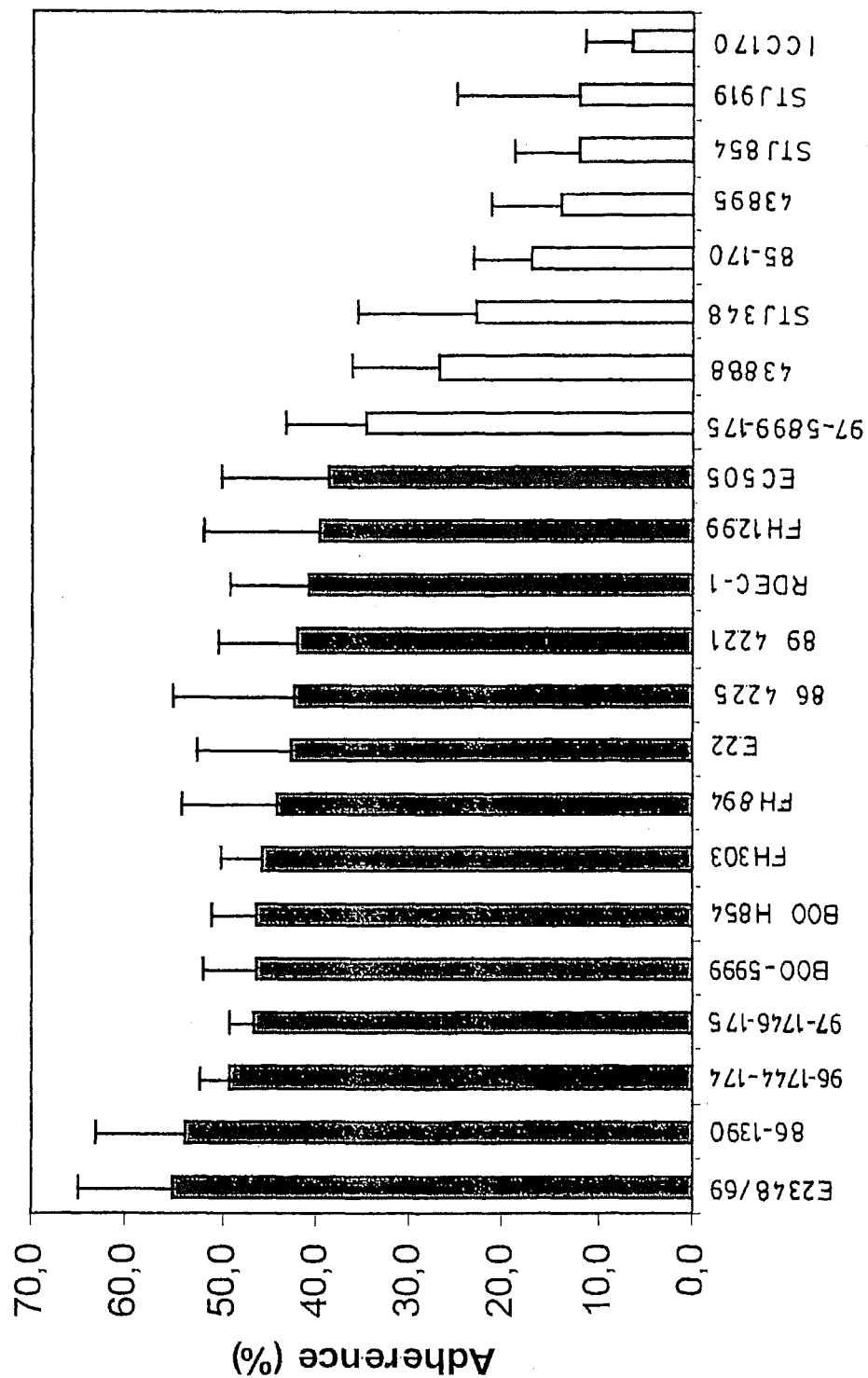
FIG. 1 is a bar graph showing that AEEC strains originating from the rabbit, pig, dog, bovine, and human (including non-O157 EHEC and EPEC), and producing Eae of the α, β, δ, or ε subtypes, induced A/E lesions equally well on newborn pig ileal explants.

As mentioned previously, the present invention relates to a new alternative approach as opposed to antibiotics for the prevention of an AEEC infection in a mammal.

More precisely, the present invention relates to antibodies immunologically specific for an AEEC virulence-associated protein, these antibodies being capable of preventing an in vivo AEEC infection when administered in a mammal. More particularly, the antibodies of the invention are capable of preventing the adhesion of the AEEC to the intestine of the mammal, and even more preferably, they prevent the development of A/E intestinal lesions associated with the AEEC.

As used herein, the term "preventing" refers to a process by which the AEEC infection is obstructed or delayed.

As used herein, the term "mammal" refers to any mammal that has the possibility of being infected by an AEEC. Among the mammals which are known to be potentially infected by an AEEC, there are humans, pigs, bovines, ovines, caprines, rabbits, dogs and cats. It will be apparent to one skilled in the art that the antibodies of the invention are intended to be immunologically specific to virulence proteins isolated form a variety of AEEC strains that may cause intestinal lesions, such as those of enteropathogenic *E. coli* (EPEC) and enterohemorrhagic *E. coli* (EHEC). Some examples of EPEC and EHEC strains are shown in Table I.

With respect to antibodies of the invention, the term "immunologically specific" refers to antibodies that bind with a relatively high affinity to one or more epitopes of a protein of interest, but which do not substantially recognize and bind molecules other than the one(s) of interest. As used herein, "antibody" and "antibodies" include all of the possibilities mentioned hereinafter: antibodies or fragments thereof obtained by purification, proteolytic treatment or by genetic engineering, artificial constructs comprising antibodies or fragments thereof and artificial constructs designed to mimic the binding of antibodies or fragments thereof. Such antibodies are discussed in Colcher et al. (*Q J Nucl Med* 1998; 42: 225-241). They include complete antibodies, F(ab')$_2$ fragments, Fab fragments, Fv fragments, scFv fragments, other fragments, CDR peptides and mimetics. These can easily be obtained and prepared by those skilled in the art. For example, enzyme digestion can be used to obtain F(ab')$_2$ and Fab fragments by subjecting an IgG molecule to pepsin or papain cleavage respectively. Recombinant antibodies are also covered by the present invention.

Alternatively, the antibody of the invention may be an antibody derivative. Such an antibody may comprise an antigen-binding region linked or not to a non-immunoglobulin region. The antigen binding region is an antibody light chain variable domain or heavy chain variable domain. Typically, the antibody comprises both light and heavy chain variable domains, that can be inserted in constructs such as single chain Fv (scFv) fragments, disulfide-stabilized Fv (dsFv) fragments, multimeric scFv fragments, diabodies, minibodies or other related forms (Colcher et al. *Q J Nucl Med* 1998; 42: 225-241). Such a derivatized antibody may sometimes be preferable since it is devoid of the Fc portion of the natural antibody that can bind to several effectors of the immune system and elicit an immune response when administered to a human or an animal. Indeed, derivatized antibody normally do not lead to immuno-complex disease and complement activation (type III hypersensitivity reaction).

Alternatively, a non-immunoglobulin region is fused to the antigen-binding region of the antibody of the invention. The non-immunoglobulin region is typically a non-immunoglobulin moiety and may be an enzyme, a region derived from a protein having known binding specificity, a region derived from a protein toxin or indeed from any protein expressed by a gene, or a chemical entity showing inhibitory or blocking activity(ies) against the AEEC virulence-associated proteins. The two regions of that modified antibody may be connected via a cleavable or a permanent linker sequence.

Since the AEEC infection is generally localized in the intestinal tract, it is highly preferable that the antibody of the invention be resistant to gastrointestinal digestion. As used herein, the term "resistant" refers to an antibody that will substantially retain its immunological function even after being in contact with gastric acids for a period of time necessary to prevent an in vivo AEEC infection. Preferably, the antibody of the invention is an avian immunoglobulin, such as IgY. Indeed, it is well known that IgY antibodies show great acid and heat resistance. The antibody of the invention may be also a human or animal immunoglobulin such as IgG1, IgG2, IgG3, IgG4, IgM, IgA, IgE or IgD carrying rat or mouse variable regions (chimeric) or CDRs (humanized or "animalized"). However, the invention is not restricted to IgY antibodies since it is conceivable that the resistance capacity of the antibody, if lacking, can be provided or increased by genetic engineering or by any other way known to one skilled in the art. Furthermore, the antibody of the invention may also be conjugated to any suitable carrier known to one skilled in the art in order to increase its resistance to gastric acids or to provide, for instance, a specific delivery and prolonged retention of the antibody, either in a targeted local area, such as the intestine, or for a systemic application.

As mentioned above, the antibody of the invention is immunologically specific to one or more AEEC virulence-associated proteins. The preferred AEEC virulence-associated proteins contemplated by the invention are Eae, Tir, EspA, Paa and immunological derivatives thereof. As used herein, the term "immunological derivative" refers to a protein/peptide that possesses an immunological activity that is substantially similar to the immunological activity of the whole protein/peptide, and such immunological activity refers to the capacity of stimulating the production of antibodies immunologically specific to an AEEC virulence-associated protein or derivative thereof. The term "immunological derivative" therefore encompass "fragments", "segments", "variants", or "analogs" of a protein/peptide.

In a highly preferred embodiment, the present invention uses IgY antibodies since and as mentioned above, they advantageously show gastric acid resistance. Furthermore, IgY antibodies have the advantage of not reacting with mammalian complement, Fc receptor, protein A or protein G. Also, IgY antibodies produced in eggs and their extraction from egg yolks can be performed on a large scale without costly investment.

In this connection and according to another aspect, the present invention is also directed to a process for obtaining the above mentioned antibody immunologically specific for an AEEC virulence-associated protein. Although, many processes known in the art may be suitable to obtain the antibodies contemplated by the inventors, it is preferable that the process of the present invention comprises the steps of: a) actively immunizing a fowl hen for eliciting the production of antibodies in an egg of the hen; and b) recovering the antibodies from the egg. A person skilled in the art will understand that the immunizing step is achieved by well known methods. For instance, the AEEC-virulence protein may be given parenterally, for example intravenously, intramuscularly, subcutaneously. As used herein, the term "fowl" refers to any birds capable of being immunized. Among those, the common domesticated chicken is preferred. The process of the invention may also comprises a step of administering at least one booster of the proteins to maintain a hyperimmune state in the hen. Furthermore, the process of the invention preferably comprises a step of purifying the antibodies from a yolk fraction of the egg. Again, the purification step is achieved with methods well known to one skilled in the art. Such a person will also understand that the boosting step is not limited to being done before the step of laying the egg. Indeed, a booster may also be given to the same hen even during or after the egg laying step.

Consequently, the present invention also relates to a fowl egg which contains an antibody of the invention. The present invention further relates to an isolated yolk of the egg.

The present invention also describes a method and compositions for the prevention of AEEC-associated diseases. Many methods could be used to practice the present invention. However, it is particularly believed that a method which comprises the step of orally administering to a mammal an antibody of the invention, a fowl egg and/or an isolated yolk as previously defined is particularly advantageous from a commercial point of view. Nevertheless, methods that involve a parenteral administration of the antibody of the invention may be considered by one skilled in the art.

According to a preferred embodiment, the composition of the invention comprises at least one element immunologically active against AEEC and a biologically acceptable vehicle or carrier. Such an element may either be an antibody, a fowl egg or an isolated yolk as defined above. For preparing the compositions of the present invention, methods well-known in the art may be used. As used herein, the term "immunologically active", or reference to the immunological activity of an element, such as an antibody of the invention, refers in that instance to the ability of such antibody to prevent an AEEC infection in a mammal by binding to an AEEC virulence-associated protein. As used herein, the term "biologically acceptable" refers to a vehicle or a carrier that can be safely administered to a mammal, particularly humans and animals, without overly negative or toxic side effects. Such vehicle or carrier may be used for various purposes, such as preserving agents, solubilizing agents, stabilizing agents, wetting agents, emulsifiers, sweeteners, colorants, odorants, salts, buffers, coating agents or antioxidants and the like. They may be readily prepared by those of skill in this art using well known methods.

According to another embodiment, the composition of the invention is formulated under the form of a pharmaceutical or a nutraceutical composition. The present invention also provides a food additive comprising at least one of the above mentioned elements and further comprises a composition as defined above. It will be clear to one skilled in the art that although the compositions of the invention are preferably administered orally, they may be administered by any other suitable route. Indeed, it is conceivable that they could be given by other means. In the case that the compositions are given orally, they may be in the form of tablets, capsules, powder, syrups, etc.

The compositions of the invention may be used in conjunction with pharmaceutical compositions known in the art. For instance, one may find it advantageous to combine one of the elements of the composition of the invention with other active agents that may be used to treat or prevent diseases others than those induced by AEEC.

The amount of specific antibodies that is administered to a human or an animal or that is present in the composition of the invention is a therapeutically effective amount. A therapeutically effective amount of antibody is that amount necessary for obtaining beneficial results without causing overly negative secondary effects in the host to which the antibody or composition is administered. Moreover, an effective amount of an antibody for treating a particular disease is an amount that is sufficient to ameliorate, or in some manner reduce the symptoms associated with the disease. Such an amount may be administered as a single dosage or may be administered according to a regimen, whereby it is effective. The amount may cure the disease but, typically, is administered in order to ameliorate the symptoms of the disease.

The exact amount of antibody or of each of the components in the composition and amount of the composition to be administered will vary according to factors such as the type of the condition to be treated, the other ingredients in the composition, the mode of administration, the age and weight of the mammal, etc. Without being bound by any particular dosage, it is believed that for instance for oral administration, a daily dosage of about 100 to about 600 mg/kg of lyophilised egg yolk containing antibodies immunologically specific for an AEEC virulence-associated protein (usually present as part of a composition as indicated above) may be suitable for preventing a mammalian AEEC infection in a typical adult. This dosage may be repeated as often as appropriate. Typically, administration may be 1 to 21 times a week. If side effects develop, the amount and/or frequency of the dosage can be reduced.

EXAMPLE

The following example is illustrative of the wide range of applicability of the present invention and is not intended to limit its scope. Modifications and variations can be made therein without departing from the spirit and scope of the invention. Although any method and material similar or equivalent to those described herein can be used in the practice for testing of the present invention, the preferred methods and materials are described.

Summary

The inventors have successfully produced egg yolk antibodies against purified fusion proteins of the known attaching and effacing virulence factors Eae, EspA, EspB, EspD, and Tir and of a new putative attaching and effacing virulence factor Paa. They have demonstrated that only the anti-Eae, anti-Tir, and anti-Paa antibodies were able to significantly block the development of attaching and effacing (A/E) lesions due to the homologous porcine E. coli strain ex vivo in the pig ileal organ culture model. These antibodies were also able to block the development of A/E lesions due to attaching and effacing E. coli originating from various other animal species such as the bovine and dog, and from humans, including both O157:H7 and non-O157:H7 E. coli. Finally, the inventors have demonstrated that the anti-Eae antibodies were able to significantly reduce the development of A/E lesions due to the homologous pig and O157:H7 human attaching and effacing E. coli in vivo in a newborn pig infection model. These results clearly demonstrate that chicken egg yolk antibodies specific for certain of the virulence factors involved in attachment and effacement are able to block bacterial infection and development of intestinal lesions in the pig and thus are a potential candidate for use in the treatment of infections caused by attaching and effacing E. coli. They are also a potential candidate as a feed additive for oral administration to cattle in order to eliminate O157:H7 and other attaching and effacing E. coli from the intestine and prevent contamination of meat and consequent infection of humans.

Materials and Methods.

Bacterial Strains, Plasmids and Media.

E. coli M155(pREP4™) (Qiagen) was used as the host strain for recombinant proteins. The porcine attaching and effacing E. coli (AEEC) P86-1390 (serogroup O45, streptomycin resistant, Sm®) was isolated at the Faculté de Médecine Vétérinaire, Saint-Hyacinthe, Québec, Canada from a 4-week-old pig with postweaning diarrhea. O45 strain P86-1390 induces typical attaching and effacing (A/E) lesions (Zhu et al., 1994 *Infect Immun* 62: 4153-4159; Zhu et al., 1995 *Can J Vet Res* 59: 118-123) and its genomic DNA was used as template to amplify the virulence factor genes carried on the locus of enterocyte effacement (LEE).

For explant model challenge (see Table 2 for strains characteristics), bacteria were grown overnight in Trypticase Soy Broth (TSB, Difco) with agitation (150 rpm) at 37° C., then transferred in Dubelcco's Modified Eagle's Medium (DMEM, GibcoBRL) and grown to early exponential phase prior to use ($OD_{600}$ 0.7, corresponding to approximately $2.0 \times 10^8$ CFU, determined by use of specific growth curves). 1% final D-Mannose was added to each broth culture to minimize Type-1 fimbriae-mediated adherence prior to infection.

Construction of Fusion Genes.

The 3' end (carboxy) or the entire (mature) eae gene, espA, espB, and espD genes, tir gene, and the 3' end (carboxy) or the entire (mature) paa gene were amplified by PCR using primer pairs listed in Table 3. The amplicons were inserted into the pGEM-T™ vector (Promega) and then introduced into the pQE-30™ expression vector (Qiagen) using the appropriate cloning site (between BamHI and SalI sites for eae carboxy, espA, espB, espD, paa carboxygenes, between BamHI and SphI for eae mature gene, and between HindIII and SacI for tir gene). Gene fusions were checked by sequencing.

Production and Purification of Fusion Proteins.

An overnight LB broth preculture was used to inoculate a 1 liter LB broth culture. Cells were grown at 37° C. with shaking until the $OD_{600nm}$ was 0.7-0.8. Isopropylthiogalactoside (IPTG) was then added to a final concentration of 1 mM. After incubation for about 4 hours, cells were harvested by centrifugation at 4000×g for 10 minutes and resuspended in two volumes of buffer A (Qiagen). Samples can be centrifuged and the pellet stored frozen at −70° C. until use. Samples were thawed at room temperature and resuspended into buffer A. One mg/ml of lysozyme and a final concentration of 100 µM of PMSF were added. The overall suspension was incubated 30 minutes on ice and sonicated. For each ml of sample, 10 µg of Rnase A and 5 µg of Dnase 1 were added and after incubation for 15 minutes on ice, the sample was clarified by centrifugation at 15000×g for 20 minutes. The supernatant was mixed with a 50% slurry of Ni-NTA resin (Qiagen) in buffer A (8 ml of slurry per liter of cells). After gentle mixing in a rotating tube for one night, the resin was added to a Qiagen column, washed with buffer A until the $OD_{280nm}$ was less than 0.01, washed with buffer B (Qiagen) until the $OD_{280nm}$ was less than 0.02, washed with 0.1 M imidazole in buffer B (20 ml per liter of cells), and eluted with 0.25 imidazole in buffer B. (10 ml per liter of cells). Fractions (1-1.5 ml), collected upon strating the 0.25 M imidazole elution, were analyzed by SDS-PAGE through 15% acrylamide. Those containing proteins of interest were pooled, quantified by the Lowry method, and stored at −70° C.

Western Immunoblotting.

His-tagged affinity column purified proteins were mixed with an equal volume of 2× Laemmli buffer, boiled for 5 minutes, applied to a 15% SDS-PAGE, and electrotransferred onto 0.2 µm nitrocellulose membrane (Bio Rad). Blots were blocked and washed with 1% bovine serum albumin (BSA) −0.1% Tween™ 20 in Tris-buffered saline (TBS), and incubated overnight with primary antibodies, including RGS-His antibody (Qiagen) and the anti-Eae, anti-EspA, anti-EspB, anti-EspD, and anti-Tir kindly provided by Dr. Gad Frankel and Dr. Frank Ebel. For chicken antibody (IgY) production analysis, purified IgY specificly directed against each of the LEE virulence factors were used as primary antibodies. Filters were then developed with secondary goat anti-rabbit (1/1000), goat anti-mouse (1/1000) or rabbit anti-chicken (1/5000) HRP-conjugated IgG and with $H_2O_2$-α-chloronaphtol as the substrate.

Immunization of Animals and Antibodies Purification.

Two to eight laying hens were immunized in their pectoral muscle at multiple sites with 50 µg of purified proteins and emulsified in incomplete Freund's adjuvant on days 1, 14, 28, 42 and 56. M15 (pREP4™) total proteins was used as negative control for anti-virulence factor IgY production. Eggs were collected from day 28 and kept at 4° C. until purification of antibodies. For the purification of antibodies, the yolks were separated from the yolk membrane and egg white, pooled and one volume of PBS 1× was added. The overall mixture was homogenized, mixed with one volume of chloroform, and centrifuged at 15000×g for 10 minutes. An orange coloured solution containing the vitellus, a yellow semi-solid emulsion of the lipids in chloroform, and a watery phase containing chicken IgY were then observed from the bottom to the top of the tube. Purified IgY were analyzed by SDS-PAGE stained with Coomassie blue and by Western immunoblotting as explained above.

ELISA.

Anti-virulence factor IgY titers in yolk eggs were determined using microtiter plates (Immulon 2HB, Dynec) precoated with 100 ng of purified proteins in carbonate buffer (pH 9.6). Purified IgY serially diluted in PBS 9pH 7.4) containing 1% BSA and 0.05% Tween 20 was added to the wells and incubated for 2 hours at 37° C. After washing thrice with PBS containing 0.05% Tween™ 20, bound antibodies were detected by adding rabbit anti-chicken IgG (1/25000) conjugated to peroxidase (Jackson Immuno Research Laboratories, Inc). After a 10 minutes enzyme-substrate reaction, the absorbance at 405 nm was read and antibody titers were expressed as the $\log_{10}$ of the reciprocal dilution. To monitor non-specific reactions, absorbances measured with IgY from chickens immunized with the total protein extract from the M14 (pREP4™) strain were subtracted from absorbances obtained with test samples.

Antibody Extraction from Egg Yolks.

Virulence factor-specific IgY was extracted from egg yolks by a method described by [Akita and Nakai, (1993) Immunol. Methods 18: 162(e): 155-164; 1993 Immunol. Methods 2: 160(2): 207-214], with some modifications. Briefly, egg yolks were separated from albumin then placed onto a towel. Egg yolks were gently rolled onto the towel to removed albumin residues, then punctured to aspirate the yolk without the vitellus. An equal volume of Phosphate Buffered Saline (PBS) was added to the yolks, then homogenized by Vortex agitation. An equal volume of chloroform was added to the solution, then mixed until there was a solid homogenate. The preparation was centrifuged for 5 minutes at 14 000 rpm, and the supernatant containing IgY was removed. The supernatant was lyophilised prior to use.

Collection and Culture of Explant Tissues.

The explant culture technique was derived from Zhu et al., 1994 (supra). Briefly, mucosal tissues from ileum were obtained from newborn colostrum-deprived piglets from a conventional herd. Piglets were tranquilized with ketamin hydrochloride before being euthanized with a pentobarbital overdose. The time lapse between death and initiation of explant cultures was approximately 1 h and each strain was tested in at least 2 piglets. Upon collection, the serosa was carefully removed and mucus was gently discarded with steril swab. Tissues were immersed in sterile complete RPMI 1640™ media (GibcoBRL), transported to the laboratory on ice, and placed on a rocking platform for 30 minutes. Prior to culture, tissues were cut into 5×5 mm pieces and placed mucosal side up onto biopsy foam pads (Curtin Matheson Scientific, Inc.) in multidish four-well Nunclon Delta™ Surface tissue culture plates (Nalge Nunc International). One tissue (now called an explant) was placed on each sponge with 1 sponge per well. Complete RPMI 1640 medium was added to wells without submerging the explants. Plates were incubated at 37° C. on a rocker (position 2,5) in 95% $O_2$ and 5% $CO_2$ atmosphere.

Inoculation and Examination of Explants.

The explants were infected three times at hourly intervals with 50 µl of broth culture (approximately $1 \times 10^7$ CFU) applied to the mucosal surface and incubated for 8 hours. To prevent bacterial overgrowth and acidic pH, hourly changes with sterile fresh complete RPMI 1640™ medium were carried out during culture starting 2 hours after initial explant infection.

Treatment with Antibodies in the Explant Model.

Broth cultures were incubated at 37° C. with an equal volume of lyophilised antibody preparation, previously reconstituted with PBS, for 30 minutes prior to explant infection.

Light Microscopy.

After culture, explants were fixed in 10% buffered formalin for microscopic examination. The same protocol was used for sections from in vivo experimentally infected newborn piglets. Formalin-fixed sections were further placed into Nylon™ tissue biopsy bags (Shandon Inc.), processed, paraffin-embedded, sectioned at 5 µm, and stained with hematoxylin, phloxine, and safranine (HPS) according to standard techniques. Sections stained with HPS were examined by light microscopy for epithelial intimate-adherent bacteria. Each intact villus was examined for the presence of intimate-adherent bacteria, and evaluation of mean epithelial surface covered with intimate-adherent bacteria was performed, according to a scale from 0 to 100%.

Immunofluorescence.

Sections on glass slides were deparaffined into xylene for 5 minutes before rehydration into progressive ethanol solutions. Sections were rinsed in PBS then antigenic binding sites were blocked in PBS-1% BSA-0.1% Tween20 solution at 37° C. for 20 minutes. Thereafter, sections were rinsed in PSB and incubated at 37° C. for 20 minutes with 1:50 dilution of primary antibodies (*Escherichia coli* Serotyping Laboratory, Canada) according to the specific strain serotype. After rinsing out into PSB, sections were incubated at 37° C. with 1:200 dilution of goat anti-rabbit FITC-conjugated secondary antibody (Jackson ImmunoResearch Laboratories inc., USA) for 20 minutes. Sections were finally counterstained with 0.2% Evan's Blue™ (Fisher Scientific Company, USA). Mounted sections were examined with a Leitz Diaplan™ microscope equipped with epifluorescence.

Transmission Electron Microscopy (TEM).

Small ileum, cecum, or colon sections (3 mm×3 mm) were fixed for 2 hours at room temperature in 2.5% (v/v) glutaraldehyde, then rinsed in cacodylate buffer (0.1M cacodylate, pH 7.3) for 1.5 hours with regular changes. Thereafter, tissues were post-fixed for 1 hour at room temperature into 2% osmium tetroxide ($OsO_4$), then rinsed into water for 1.5 hours with regular changes, dehydrated in graded ethanol series, and finally embedded in Spurr resin (Marivac, Nova Scotia, Canada). Thin sections were mounted on copper grids, stained with uranyl acetate and lead citrate, and examined for AE lesions with a Philips 420™ transmission electron microscope at 80 kV (Philips Electronics, The Netherlands).

Piglet Infection and Antibody Challenges In Vivo.

22 newborn piglets from a conventional herd were used to assay effects of anti-eaeM antibodies on bacterial adherence in vivo. 12 piglets were colostrum-deprived prior to infection with porcine strain 1390, while the other 10 piglets were colostrum-fed prior to infection with human EHEC strain 85-170. All piglets were kept in cages, and fed with evaporated milk during the experiment. Group 1 (1390 infection)

piglets were infected with 1×10¹⁰ CFU of 1390 EPEC strain in 2 ml of TSB broth for 2 days, and received twice a day egg yolks from hens immunized with sonicate of PREp15 strain as a adherence positive control (n=6), or egg yolks from hens immunized with EaeM fusion protein (n=6). Group 2 (85-170 infection) piglets were infected with 1×10¹⁰ CFU of 85-170 EHEC strain in 2 ml of TSB broth for 2 days, and received three times a day, lyophilized egg yolks reconstituted in milk from hens immunized with a sonicate of PREp4 strain as an adherence positive control (n=5), or lyophilized egg yolks reconstituted in milk from hens immunized with EaeM fusion protein (n=5). Piglets were monitored daily for any clinical signs of diarrhea, and were necropsied at 48 hours after the initial infection. Piglets were tranquilized with ketamine hydrochloride, then euthanized with an overdose of pentobarbital solution.

Results and Discussion a) Production of Fusion Proteins

It has clearly been demonstrated in the literature that the intimin (Eae) and the secreted proteins Tir (Translocated intimin receptor), EspA, EspD and EspB are virulence factors playing an important role in the pathogenesis of various AEEC infections and could elicit an antibody response. Furthermore, the inventors have discovered a new protein called Paa (for Porcine attaching and effacing associated) that is also involved in AEEC adhesion to host cells (see section d). These different virulence factors were thus considered as good candidates for protective immunity and/or as markers in a diagnostic test. Also, it was considered that it would be important to produce a fusion protein by using only the C-terminal end of intimin (Eae carboxy) which is involved in receptor recognition. Thus, seven (7) fusion proteins were produced corresponding to the listed proteins in the pQE30 expression vector which links in frame a His6 tag at the N-terminal end of the proteins. Primer pairs specific for each of the virulence factors were chosen to amplify by PCR the entire (Eae, EspA, EspB, EspD, Paa, Tir) or a part (Eae carboxy) of the proteins from genomic DNA of enteropathogenic *E. coli* porcine strain 1390. The fusion proteins were detected by Western blot analysis revealed with anti-histidine antibodies and with antibodies specifically directed against each of the virulence factors. However, the His-Paa protein was only detected in low quantity. Since Paa is predicted to be unstable by the EXPASY program, a fusion with the stable C-terminal end of Paa (Paa carboxy) was carried out.

All fusion proteins were then produced on a large scale and purified on a nickel affinity column in sufficient quantities for immunization of chickens and for use as antigens in the ELISA. The purified His-Eae carboxy, His-Eae, His-EspA, His-EspB, His-EspD, His-Paa and His-Tir proteins were obtained.

b) Production and Purification of the Egg Yolk Antibodies

The immunization of chickens and the antibody purification technique were carried out from modified techniques as described in the Materials and Methods. SDS-PAGE analysis demonstrated production of IgY as early as 28 days after initial immunization with proteins His-Eae carboxy, His-Eae, His-EspA, His-EspB, His-EspD, His-Paa and His-Tir.

c) Sensitivity and the Specificity of the Egg Yolk Antibodies Against Each of the Proteins Western blot analysis showed that purified IgY recognized homologous fusion proteins. The titer of the specific IgY for each protein was then measured by ELISA using homologous purified proteins as the antigen. The ELISA test conditions were determined for each antigen and results showed a high titer (>1/25000) for each specific IgY after 42 days. The capacity of each antibody to detect the corresponding native antigen in the homologous strain 1390 and in AEEC strains from different animal species was also examined. However it appeared that the tested conditions and/or the antigen presentation did not favor the detection by ELISA of some virulence factors such as Eae or Paa in wild type bacteria.

d) Capacity of Specific Antibodies to Prevent the Development of A/E Lesions In Vitro in the Pig Ileal Organ Culture Model Elaboration of the Model The first step of this work was to determine the explant culture conditions which would allow AEEC adherence to ileal and cecal epithelial cells of weaned piglets. Different conditions were tested and a rapid technique for microscopic analysis of tissue sections by light microscopy and confirmation by electron microscopy, was set up (see Materials and Methods). A greater and more consistent adherence of the 1390 strain was observed on Ileal explants from newborn piglets than on explants from weaned pigs. Hence, the newborn pig explant model was used in subsequent experiments.

The inventors have demonstrated that AEEC strains originating from the rabbit, pig, dog, bovine, and human (including non-O157 EHEC and EPEC), and producing Eae of the α, β, δ, or ε subtypes, induced A/E lesions equally well on newborn pig ileal explants (FIG. 1). More specifically, FIG. 1 shows the mean percentage of intact villi showing bacterial adherence on ileal explant sections. Strains from various animal species and from humans show a similar percentage adherence, when compared to the homologous porcine 1390 AEEC strain, except those from O157:H7 serotype (EC505, 43888, STJ348, 85-170, 43895, STJ854, and STJ919 on the graph). All except O157:H7 strains are significantly different from eae-mutant strain ICC-170 (negative control). These data validate our model for the study of the attaching and effacing phenotype expression for both homologous and heterologous strains, except for those belonging to O157:H7 serotype. Results are presented as the mean±the standard deviation of the mean.

Figure 2:
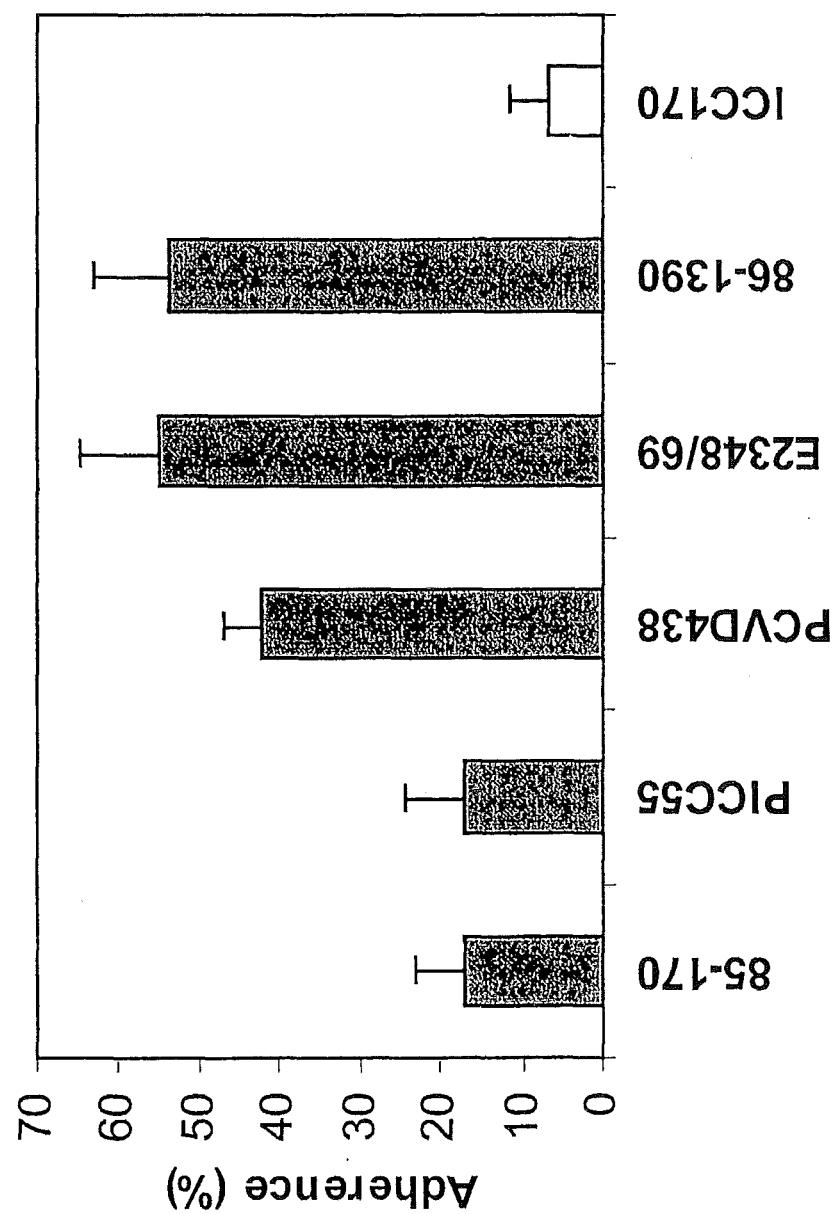
FIG. 2 is a bar graph showing that a replacement of the Eae of the γ subtype by the Eae of the α subtype in an O157:H7 strain resulted in induction of A/E lesions to a similar extent as observed for the homologous porcine AEEC strain.

On the other hand, O157:H7 AEEC strains producing Eae of the γ subtype adhered to a much lesser extent to the ileal epithelium. However, replacement of the Eae of the γ subtype by the Eae of the a subtype in an O157:H7 strain resulted in induction of A/E lesions to a similar extent as observed for the homologous porcine AEEC strain (FIG. 2). More specifically, FIG. 2 shows the effects of intimin subtype switch from gamma to alpha on the mean percentage of intact villi showing bacterial adherence of the human O157:H7 strain 85-170 on ileal explant sections. Complemented double-mutant strain PCVD-438 (intimin alpha from human E2348169 EPEC strain) shows similar adherence as homologous porcine strain 1390. PICC-55 is a gamma-intimin subtype complemented mutant strain (similar to the wild strain 85-170). These data confirm the problem of gamma-intimin subtype in adhering to the ileal explant model. Results are presented as the mean±the standard deviation of the mean. These results also suggest that Eae of the γ subtype of O157:H7 strains recognizes receptors on porcine ileal epithelial cells less well than the Eae of the other known subtypes. Nevertheless, these results confirm that pig ileal explants are an appropriate model for the examination of the effect of specific antibodies on the formation of A/E lesions by AEEC of diverse origin.

Blocking of A/E Lesions

Figure 3:
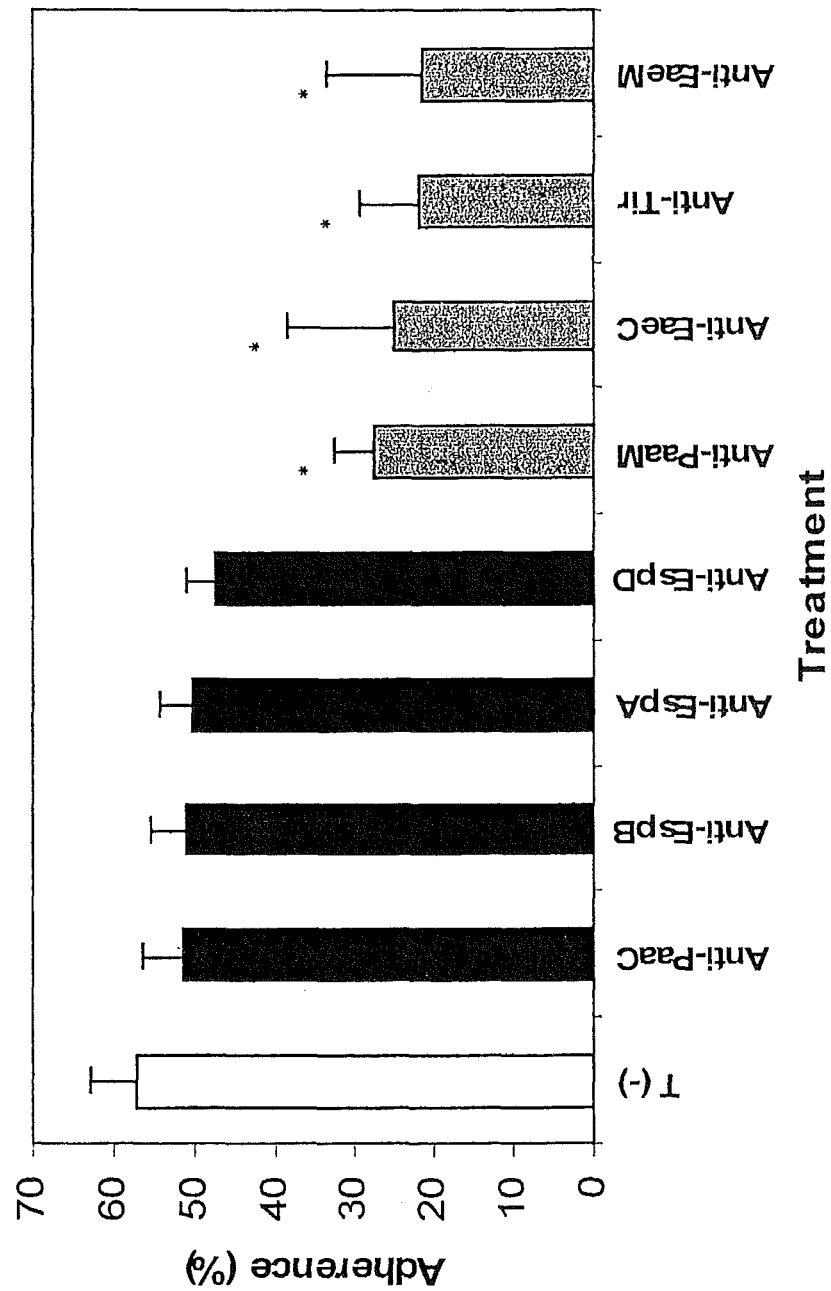
FIG. 3 is a bar graph showing that antibodies according to a preferred embodiment of the invention are able to significantly block the development of A/E lesions in ileal explants caused by the homologous strain 1390.

The capacity of the specific antibodies to prevent the development of A/E lesions ex vivo in the pig explant culture model and in vivo in the newborn pig infection model was tested with the homologous porcine strain 1390 and different heterologous AEEC strains. The results showed that the antibodies specific for the mature and carboxy terminal of Eae, Tir and Paa, in the case of the homologous porcine strain 1390, are able to significantly block the development of A/E lesions in ileal explants, for the homologous strain 1390 (FIG. 3). More specifically, FIG. 3 shows the effect of antibodies on mean percentage of intact villi showing adherence when infected by porcine strain 1390. 1390 anti-T(−) is a positive control for adherence. Results show a significant decrease in bacterial adherence (* on top of column) with anti-EaeC, anti-EaeM, anti-Tir, and anti-PaaM. Results are presented as the mean±the standard deviation of the mean. A Kruskal-Wallis test was performed with commercially available software, and post hoc 2-by-2 comparisons were done to assess differences between the groups; $P<0.0001$ was taken to be significant.

Figure 6:
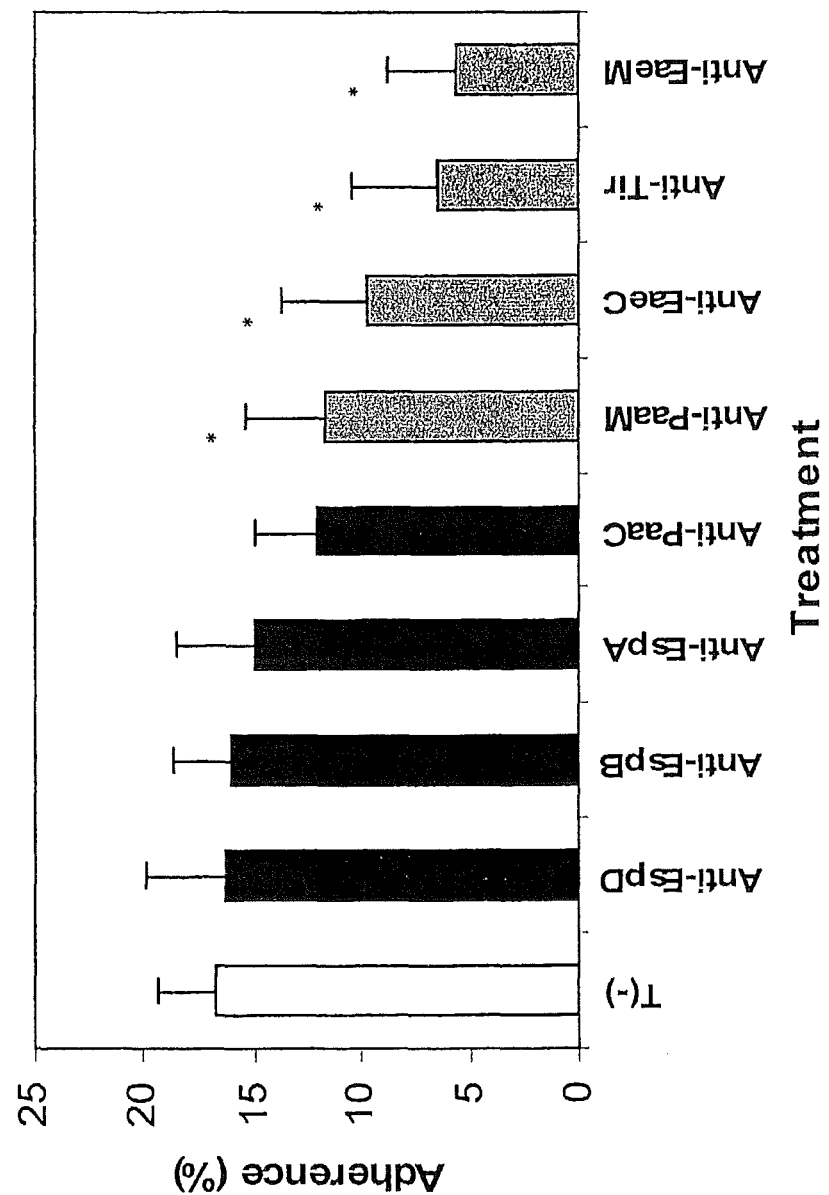
Figure 7:
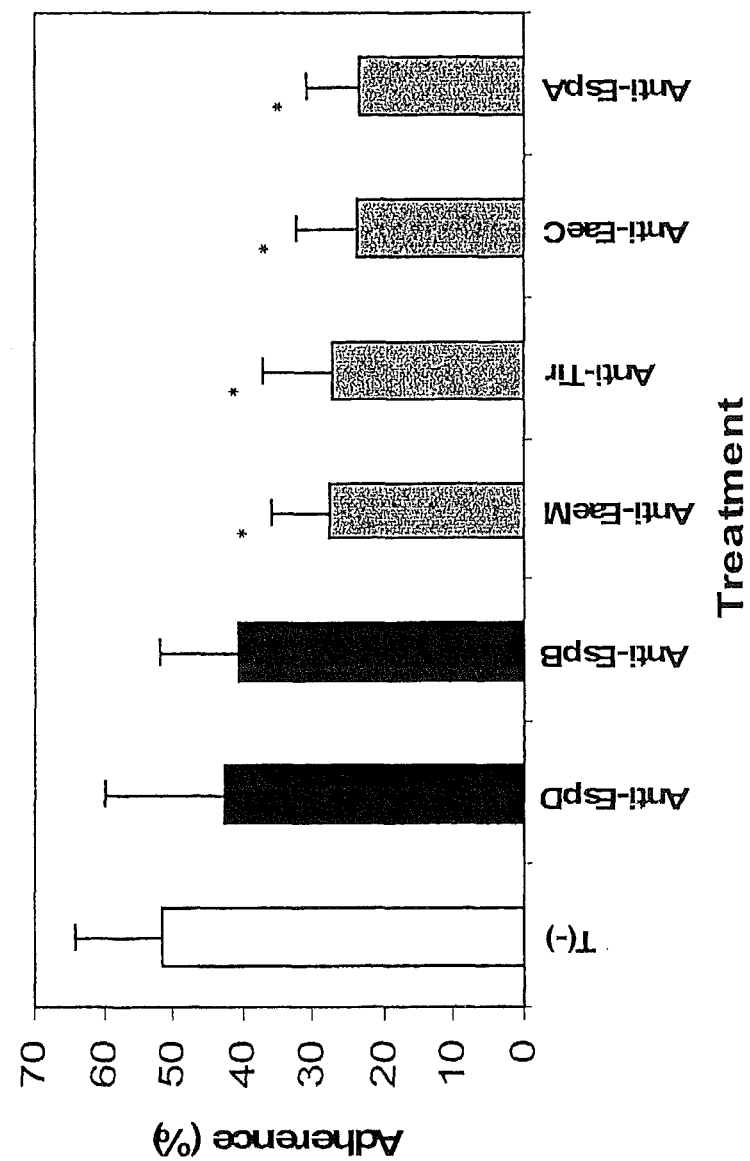
FIG. 7 is a bar graph showing that antibodies according to a preferred embodiment of the invention are able to significantly block the development of A/E lesions in ileal explants caused by various EPEC strains.

The results show that the antibodies specific for the mature and carboxy terminal of Eae, Tir and Paa, in the case of the homologous porcine strain 1390, are able to significantly block (* on top of column) the development of A/E lesions in Ileal explants for all of the tested AEEC strains from the calf (FIG. 4), and human, the latter including both O157:H7 EHEC (FIGS. 5 and 6) and EPEC strains (FIG. 7). The anti-EspA, anti-EspB, and anti-EspD antibodies did not affect the development of A/E lesions by any of the tested AEEC strains, with the exception of a human EPEC strain, for which the anti-EspA antibodies did significantly block the development of A/E lesions (FIG. 7). Anti-Paa antibodies did not block the development of A/E lesions due to this human EPEC strain which produced Eae but not Paa. Hence, the anti-Eae mature, anti-Tir, and anti-Paa antibodies, and possibly the anti-EspA antibodies, were considered as potential candidates for the blocking of development of A/E lesions in vivo.

Figure 4:
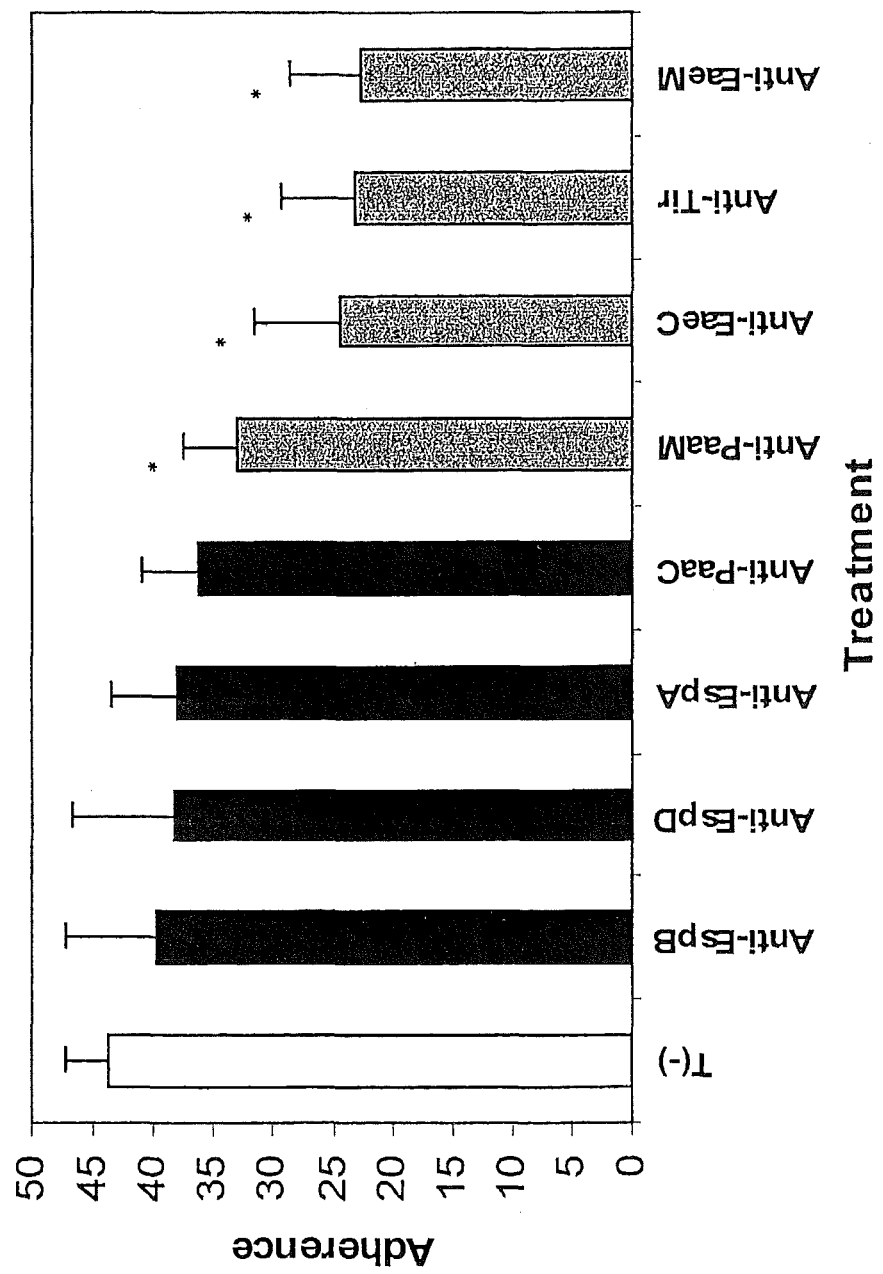
FIG. 4 is a bar graph showing that antibodies according to a preferred embodiment of the invention are able to significantly block the development of A/E lesions in ileal explants caused by various calf AEEC strains.

More specifically, FIG. 4 shows the effect of antibodies on mean percentage of intact villi showing adherence when infected by bovine strain B00-H854. B00-H854 represents the strain alone, whereas B00-H854 anti-T(−) is a positive control for adherence. Results show a significant decrease in bacterial adherence (*on top of column) with anti-EaeC, anti-EaeM, and anti-Tir, and, to a lesser extent, with anti-PaaM. Results are presented as the mean±the standard deviation of the mean. A Kruskal-Wallis test was performed with commercially available software, and post hoc 2-by-2 comparisons were done to assess difference between the groups; $P<0.0001$ was taken to be significant.

Figure 5:
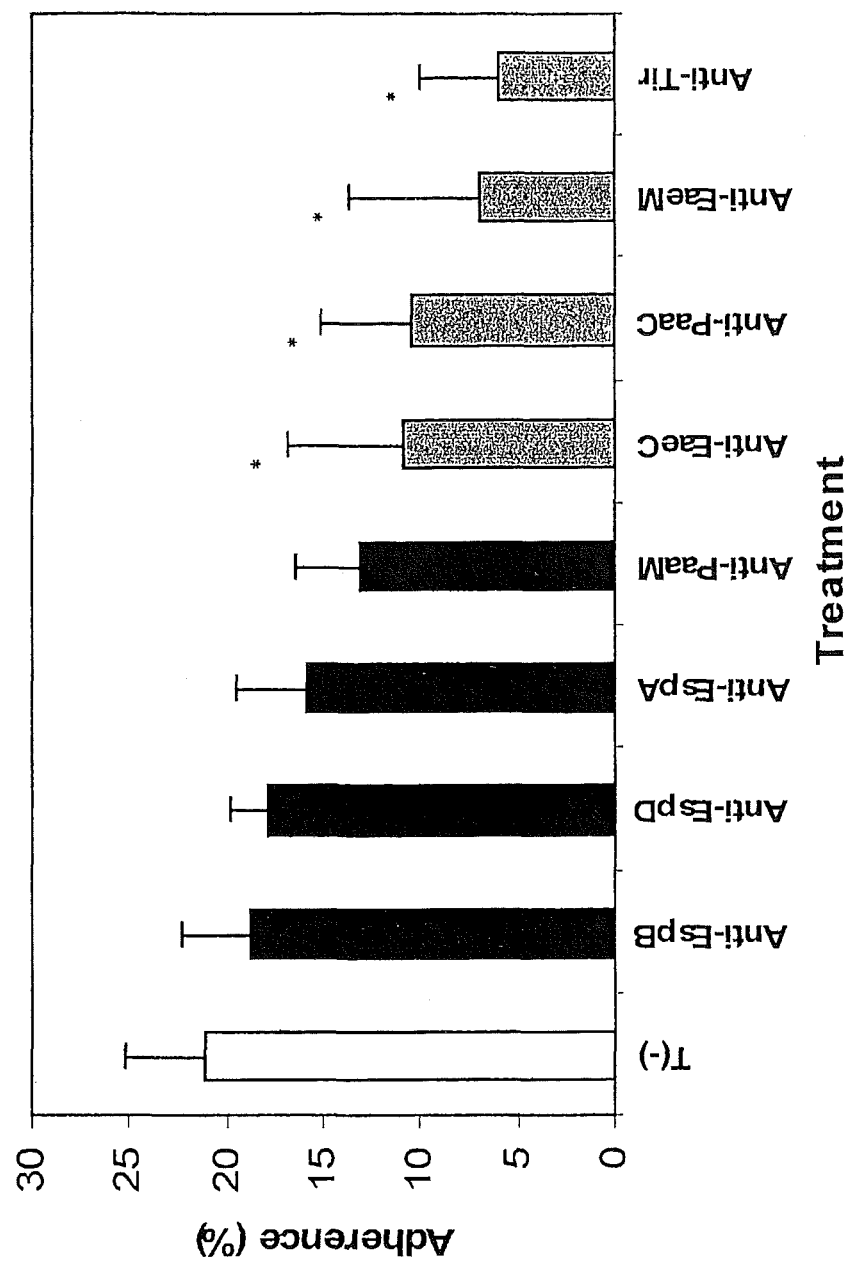
FIGS. 5 and 6 are bar graphs showing that antibodies according to a preferred embodiment of the invention are able to significantly block the development of A/E lesions in ileal explants caused by various human AEEC strains.

FIG. 5 shows the effect of antibodies on mean percentage of intact villi showing adherence when infected by human O157:H7 EHEC strain STJ348. STJ348 represents the strain alone, whereas STJ348 anti-T(−) is a positive control for adherence, and ICC-170 is an eae-mutant strain used as a negative control. Results show a significant decrease in bacterial adherence (* on top of column) with anti-Tir, anti-EaeM, and, to a lesser extent, with anti-PaaC and anti-EaeC. Results are presented as the mean±the standard deviation of the mean. A Kruskal-Wallis test was performed with commercially available software, and post hoc 2-by-2 comparisons were done to assess difference between the groups; $P<0.0001$ was taken to be significant.

FIG. 6 shows the effect of antibodies on mean percentage of intact villi showing adherence when infected by human O157:H7 EHEC strain 85-170. 85-170 represents the strain alone, whereas 85-170 anti-T(−), is a positive control for adherence, and ICC-170 is an eae-mutant strain used as a negative control. Results show a significant decrease in bacterial adherence (*on top of column) with anti-EaeM, anti-Tir, and, to a lesser extent, with anti-EaeC and anti-PaaM. Results are presented as the mean±the standard deviation of the mean. A Kruskal-Wallis test was performed with commercially available software, and post hoc 2-by-2 comparisons were done to assess difference between the groups; $P<0.0001$ was taken to be significant.

Figures 8A, 8B:
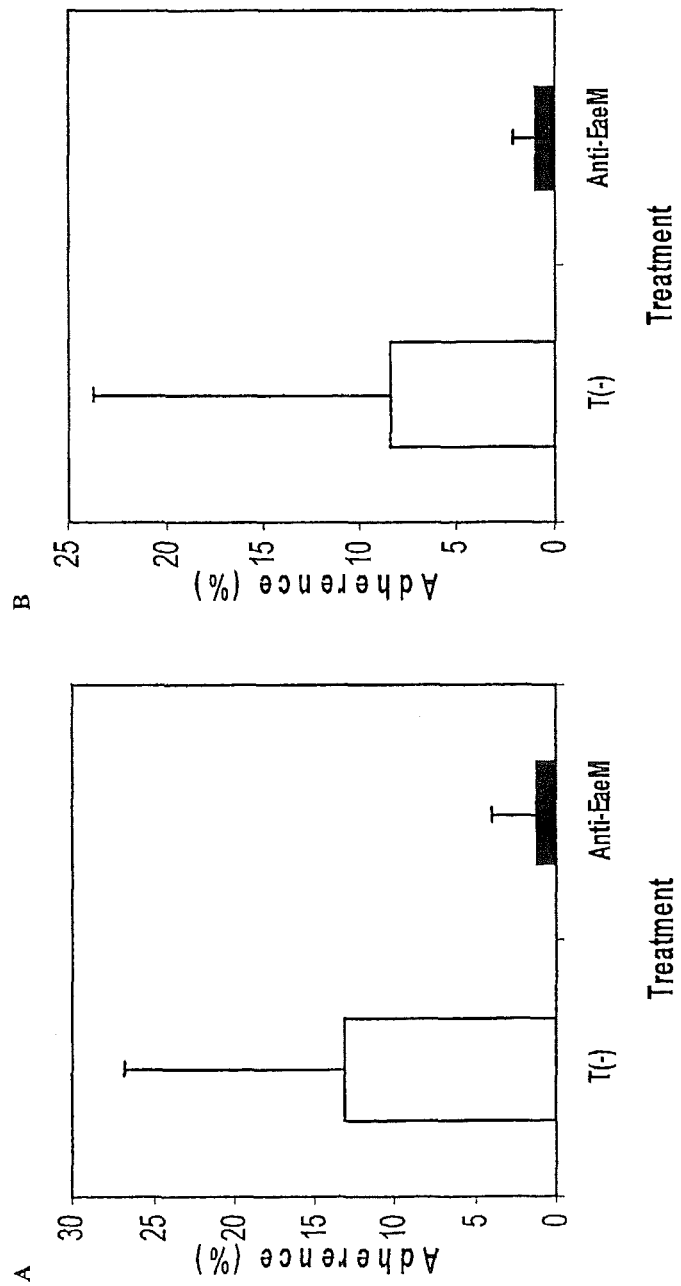
FIGS. 8A and 8B are bar graphs showing that oral administration of egg yolk antibodies according to a preferred embodiment of the invention significantly inhibit the development of A/E lesions in the cecum and colon of piglets challenged with an homologous porcine AEEC strain.

Moreover, FIG. 7 shows the effect of antibodies on mean percentage of intact villi showing adherence when infected by human EPEC strain E2348169. E2348169 represents the strain alone, whereas E2348/69 anti-T(−) is a positive control for adherence. Results show a significant decrease in bacterial adherence (*on top of column) with anti-EspA, anti-EaeC, anti-Tir, and anti-EaeM. Results are presented as the mean±the standard deviation of the mean. A Kruskal-Wallis test was performed with commercially available software, and post hoc 2-by-2 comparisons were done to assess difference between the groups; $P<0.0001$ was taken to be significant.

e) Ability of Appropriate Ego Yolk Antibodies to Prevent the Development of Intestinal Colonization and Diarrhea In Vivo in the Newborn and Weaned Pig Experimental Infection Models Since in vivo challenge experiments in pigs are costly and time-consuming, the is inventors have decided to focus on the evaluation of the effect of the anti-Eae antibodies on the development of A/E lesions in vivo, Using the colostrum-deprived newborn piglet model, it was demonstrated that oral administration of the purified anti-Eae egg yolk antibodies significantly inhibited the development of A/E lesions in the cecum and colon of piglets challenged with the homologous porcine AEEC strain (FIGS. 8A and 8B). More specifically, FIG. 8A shows antibody effects in the cecum, whereas FIG. 8B shows antibody effects in the colon. Anti-T(−) results are from piglets (n=6) that received egg yolks from non-immunized hens, and represent a positive control for adherence, whereas anti-EaeM represent piglets (n=6) that received egg yolks containing anti-EaeM antibodies directed against mature intimin. Results show a significant decrease in bacterial adherence with anti-EaeM, when compared with anti-T (−). Results are presented as the mean±the standard deviation of the mean. Statistical analysis is still in progress.

Figures 9A, 9B:
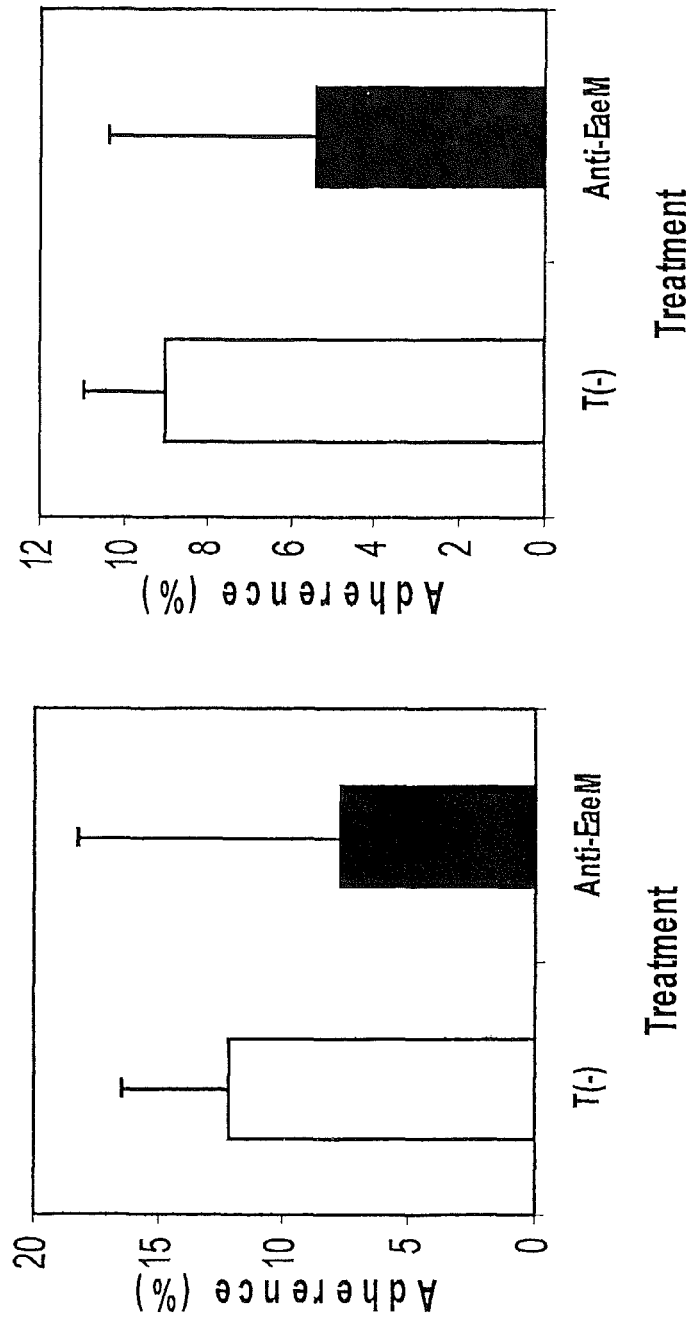
FIGS. 9A and 9B are bar graphs showing that oral administration of egg yolk antibodies according to a preferred embodiment of the invention inhibit the development of A/E lesions in the cecum and colon of piglets challenged with an O157:H7 AEEC strain.

Since O157:H7 AEEC strains are an important cause of problems in humans, it was decided to also focus on the evaluation of the effect of the anti-Eae antibodies on the development of A/E lesions in vivo in an O157:H7 pig challenge model. It has been previously shown that O157:H7 strains induce A/E lesions to a greater extent in colostrum-fed rather than in colostrum-deprived piglets. Using a colostrum-fed 3-day-old pig model, the inventors have demonstrated that oral administration of the purified anti-Eae egg yolk antibodies also inhibited the development of A/E lesions in the cecum and colon of piglets challenged with an O157:H7 AEEC strain (FIGS. 9a and 9B). More specifically, FIG. 9A shows antibody effects in the cecum, whereas FIG. 9B shows antibody effects in the colon. Anti-T(−) results are from piglets (n=5) that received lyophilised egg yolks from non-immunized hens, and represent a positive control for adherence, whereas anti-EaeM represents piglets (n=5) that received lyophilised egg yolks containing anti-EaeM antibodies directed against mature intimin. Results show a decrease in bacterial adherence with anti-EaeM, when compared with anti-T(−). Results are presented as the mean±the standard deviation of the mean. Statistical analysis is still in progress.

CONCLUSION

Hence, the inventors have shown, for the first time, that orally administered antibodies specific for AEEC virulence-associated protein, such as the adhesin Eae, are able to inhibit the development of A/E lesions in the live animal. In addition, they have showed that antibodies specific for the Eae of the β subtype and produced by an AEEC of pig origin are able to inhibit the development of A/E lesions due to an O157:H7 AEEC of human origin that produces Eae of they subtype.

Altogether, these ex vivo and in vivo results show that antibodies specific for the Eae and Tir of the porcine AEEC are useful for the inhibition of development of A/E lesions due to AEEC infections in the various animal species and in humans. Antibodies specific for Pea are useful, at least, for the inhibition of development of A/E lesions due to the AEEC homologous to the strain used for preparation of the Paa antibodies.

TABLE 1

Serogroups and serotypes of AEEC

Human EHEC

| | |
|---|---|
| Serogroup | O157, O111, O26 |
| Serotype | O4.H-; O5.H-; O16.H6; O26.H11; O26.H21; O26.H32; O46.H31; O48.H21; O55.H7; O91.H10; O91.H21; O98.H-; O111.H2; O111.H8; O111.H-; O113.H21; O117.H14; O118.H12; O119.H6; O125.H-; O126.H8; O128.H2; O145.H-; O157.H7; O157.H-; O172.H-. |

Human EPEC

| | |
|---|---|
| Serogroup | O26, O55, O111, O119, O125, O126, O127, and O128 |
| Serotype | O18a,c.H7; O20.H26; O20.H34; O25.H1; O26.H11; O26.H-; O44.H34; O55.H6; O55.H7; O55.H-; O86.H27; O86.H34; O86.H-; O91.H7; O91.H-; O111.H2; O111.H12; O111.H-; O114.H10; O114.H32; O119.H6; O119.H-; O125.H21; O125.H-; O126.H2; O126.H-; O127.H9; O127.H21; O127.H40; O127.H-; O128.H2; O128.H7; O128.H8; O128.H12; O128.H-; O142.H6; O158.H23. |

Rabbit EPEC

| | |
|---|---|
| Newborn rabbit serogroup | O2, O8, O15, O103, O109 |
| Weaned rabbit serogroup | O15, O20, O25, O103, O109, O128, O132 |

Pig EPEC

| | |
|---|---|
| Serogroup | O45. O103, O108, NT |

Cattle EPEC

| | |
|---|---|
| Serogroup | O5, O26, O11, O118 |

TABLE 2

Bacterial strains, and characteristics

| Bacterial strains | Description and origin | Serotype | Genetic characteristics |
|---|---|---|---|
| P86-1390 | Porcine EPEC | O45 | eaeβ+, espA+, tir+, paa+ |
| C89-4221 | Canine EPEC | O112ab | eaeα+, espA+, tir+, paa+ |
| C86-4225 | Canine EPEC | O49 | eaeδ+, espA+, tir+, paa+ |
| RDEC-1 | Rabbit EPEC | O15:NM | eaeβ+, espA+, tir+, paa+ |
| E22 | Rabbit EPEC | O103:H2 | eaeβ+, espA+, tir+, paa+ |
| 97-5899-175 | Rabbit EPEC | Non-typable | eaeβ+, espA+, tir+, paa- |
| 96-1744-174 | Rabbit EPEC | Non-specific typing | eaeβ+, espA+, tir+, paa+ |
| 97-1746-175 | Rabbit EPEC | O55 | eaeβ+, espA+, tir+, paa+ |
| E2348/69 | Human EPEC | O127:H6 | eaeα+, espA+, tir+, paa- |
| STJ348 | EHEC | O157:H7 | eaeγ+, espA+, tir+, paa+ |
| EC505 | EHEC | O157:H7 | eaeγ+, espA+, tir+, paa+ |
| STJ919 | EHEC | O157:H7 | eaeγ+, espA+, tir+, paa+ |
| STJ854 | EHEC | O157:H7 | eaeγ+, espA+, tir+, paa+ |
| 43888 | EHEC, negative for vt genes | O157:H7 | eaeγ+, espA+, tir+, paa+ |
| 43895 | EHEC | O157:H7 | eaeγ+, espA+, tir+, paa+ |
| 85-170 | EHEC isolate from United States, cured of phage encoding verotoxin | O157:H7 | eaeγ+, Δvt-, espA+, tir+, paa+ |
| ICC-170 | EHEC | O157:H7 | Δeae-, Δvt-, espA+, tir+, paa+ |
| PCVD-438 | EHEC | O157:H7 | eaeα+$^c$, Δvt-, espA+, tir+, paa+ |
| PICC-55 | EHEC | O157:H7 | eaeγ+$^c$, Δvt-, espA+, tir+, paa+ |
| B00-H854 | Bovine EPEC | O45 | eaeϵ+, espA+, tir+, paa+ |
| B00-5999 | Bovine EPEC | O26 | eaeβ+, espA+, tir+, paa+ |
| FH1299 | Non-O157 EHEC | O26 | eaeβ+, espA+, tir+, paa+ |
| FH894 | Non-O157 EHEC | O45 | eaeϵ+, espA+, tir+, paa+ |
| FH303 | Non-O157 EHEC | O103 | eaeϵ+, espA+, tir+, paa+ |

TABLE 3

Primers and PCR products

| Genes | Sequence of primers 5'-3' | Amplicon size (bp) |
|---|---|---|
| Eae carboxy | F GGATCCGCAACAACCGATCAGAAT (SEQ ID NO: 1) | 702 |
| | R CTCGAGTTTT ACACAAACAG GAAA (SEQ ID NO: 2) | |
| Eae mature | F GGATCCAATGGTGAAAAT (SEQ ID NO: 3) | 2712 |
| | R AAGCTTTTTTACACAAACAGG (SEQ ID NO: 4) | |
| EspA | F GGATCCATGGATACATCAACTGCA (SEQ ID NO: 5) | 585 |
| | R CTCGAGTTTACCAAGGGATA (SEQ ID NO: 6) | |
| EspB | F GGATCCATGAATACTATTGATTAT (SEQ ID NO: 7) | 954 |
| | R CTCGAGAACCAGCTAAGCGAACCGA (SEQ ID NO: 8) | |
| EspD | F GGATCCATGCTTAATGTAAATAGC (SEQ ID NO: 9) | 1152 |
| | R CTCGAGAACTCGACCACTAACAAT (SEQ ID NO: 10) | |
| Tir | F GAGCTCATGCCTATTGGTAAT (SEQ ID NO: 11) | 1626 |
| | R AAGCTTAACGAAACGTGCGG (SEQ ID NO: 12) | |
| Paa carboxy | F GGATCCCTTTATCTGCGAAAAA (SEQ ID NO: 13) | 488 |
| | R CTCGAGAGTGCCTTTCCTGG (SEQ ID NO: 14) | |
| Paa mature | F GGATCCATGAGGAACATAA (SEQ ID NO: 15) | 765 |
| | R CTCGAGAGTGCCTTTCCTGG (SEQ ID NO: 16) | |

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention as defined in the claims.

The invention claimed is:

1. A method for preventing the development of attaching and effacing (A/E) intestinal lesions associated with an attaching and effacing *Escherichia coli* (AEEC) in a mammal, said method comprising: passive immunization by oral administration to the mammal of IgY antibodies immunologically specific to AEEC virulence-associated proteins, wherein the IgY antibodies are a mixture of an IgY antibody immunologically specific to porcine attaching-effacing associated protein Paa and one or more IgY antibodies immunologically specific to an AEEC virulence-associated protein selected from the group consisting of intimin (Eae), translocated intimin receptor (Tir) and secreted protein EspA, and wherein the antibodies prevent the development of A/E intestinal lesions associated with an AEEC in the mammal.

2. The method of claim 1, wherein the IgY antibodies are isolated and purified.

3. The method of claim 1, wherein the antibodies are combined with a biologically acceptable vehicle or carrier.

4. The method of claim 1, wherein the IgY antibodies are comprised in an egg.

5. The method of claim 1, wherein the IgY antibodies are comprised in an isolated yolk of an egg.

6. The method of claim 4, wherein the egg is lyophilized and is administered in a powdered form.

7. The method of claim 5, wherein the isolated yolk is lyophilized and is administered in a powdered form.

8. The method of claim 1, wherein one of the IgY antibodies is immunologically specific to the AEEC virulence-associated protein Tir.

9. The method of claim 1, wherein one of the IgY antibodies is immunologically specific to the AEEC virulence-associated protein EspA.

10. The method of claim 1, wherein one of the IgY antibodies is immunologically specific to the AEEC virulence-associated protein Eae.

11. The method of claim 1, wherein the IgY antibodies are a mixture of an antibody immunologically specific to Paa, an antibody immunologically specific to Eae, an antibody immunologically specific to Tir and an antibody immunologically specific to EspA.

* * * * *

UNITED STATES PATENT AND TRADEMARK OFFICE
CERTIFICATE OF CORRECTION

PATENT NO. : 8,623,372 B2  Page 1 of 1
APPLICATION NO. : 12/732419
DATED : January 7, 2014
INVENTOR(S) : Fairbrother et al.

It is certified that error appears in the above-identified patent and that said Letters Patent is hereby corrected as shown below:

In the Specification
Column 14, Line 67: Correct "Eae of they subtype."
to read -- Eae of the $\gamma$ subtype. --

Signed and Sealed this
Thirtieth Day of September, 2014

Michelle K. Lee
*Deputy Director of the United States Patent and Trademark Office*